(12) United States Patent
Kitamura et al.

(10) Patent No.: US 7,805,275 B2
(45) Date of Patent: Sep. 28, 2010

(54) TRAVELING DIRECTION MEASURING APPARATUS AND TRAVELING DIRECTION MEASURING METHOD

(75) Inventors: Toru Kitamura, Tokyo (JP); Masaya Yamashita, Tokyo (JP)

(73) Assignee: Asahi Kasei EMD Corporation, Tokyo (JP)

( * ) Notice: Subject to any disclaimer, the term of this patent is extended or adjusted under 35 U.S.C. 154(b) by 457 days.

(21) Appl. No.: 11/887,281

(22) PCT Filed: Mar. 28, 2006

(86) PCT No.: PCT/JP2006/306279

§ 371 (c)(1),
(2), (4) Date: Sep. 27, 2007

(87) PCT Pub. No.: WO2006/104140

PCT Pub. Date: Oct. 5, 2006

(65) Prior Publication Data

US 2009/0143972 A1    Jun. 4, 2009

(30) Foreign Application Priority Data

Mar. 28, 2005    (JP)    ............................. 2005-093175

(51) Int. Cl.
*G01C 21/10* (2006.01)
(52) U.S. Cl. ........................ 702/150; 702/141; 702/149; 702/160; 701/200; 701/206; 701/207; 377/24.2; 73/1.37; 73/1.38
(58) Field of Classification Search .................. 702/141, 702/149–150, 160; 701/200, 206–207; 377/24.2; 73/1.37, 1.38
See application file for complete search history.

(56) References Cited

U.S. PATENT DOCUMENTS 7,457,705 B2 * 11/2008 Takahashi et al. ........... 701/211
2003/0191582 A1 * 10/2003 Terada ........................ 701/207

(Continued)

FOREIGN PATENT DOCUMENTS

JP    9-89584    4/1997

(Continued)

OTHER PUBLICATIONS

Official Notice of Rejection, dated Jul. 30, 2009 in corresponding Korean Patent Application No. 10-2007-7022029.

*Primary Examiner*—Sujoy K Kundu
(74) *Attorney, Agent, or Firm*—Finnegan, Henderson, Farabow, Garrett & Dunner, LLP

(57) ABSTRACT

A traveling direction measuring apparatus including 3-axes acceleration detecting means for detecting acceleration, and acceleration data acquiring means for repeatedly obtaining 3-axes acceleration data, said 3-axes acceleration varying with walking of a pedestrian, the traveling direction measuring apparatus including means for calculating, when the pedestrian is walking with holding said traveling direction measuring apparatus in a generally fixed attitude, gravity acceleration by averaging acceleration data sets during several steps obtained by said acceleration data acquiring means, means for calculating frequency components corresponding to duration of one step of the acceleration data sets projected on a plane perpendicular to the calculated gravity acceleration, and means for estimating a moving direction of the pedestrian seen from a terminal coordinate system associated with said traveling direction measuring apparatus according to frequency components.

1 Claim, 8 Drawing Sheets

U.S. PATENT DOCUMENTS

2008/0190201 A1 * 8/2008 Makino ....................... 73/510

FOREIGN PATENT DOCUMENTS

| JP | 11-42220 | 2/1999 |
|----|----------|--------|
| JP | 2000-97722 | 4/2000 |
| JP | 2002-139340 | 5/2002 |
| JP | 2002-263086 | 9/2002 |
| JP | 2003-302419 | 10/2003 |
| JP | 2004-138513 | 5/2004 |
| JP | 2005-114537 | 4/2005 |

* cited by examiner

TRAVELING DIRECTION MEASURING APPARATUS AND TRAVELING DIRECTION MEASURING METHOD

TECHNICAL FIELD

The present invention relates to a traveling direction measuring apparatus and traveling direction measuring method, and more particularly to a traveling direction measuring apparatus and traveling direction measuring method usable as a pedestrian navigation system in a mobile terminal including a geomagnetic sensor and acceleration sensor in locations where it is difficult to obtain high positioning accuracy such as inside buildings or around multistory buildings where GPS (Global Positioning system) cannot be used.

BACKGROUND ART

Recently, small-sized mobile terminals with a GPS function, typified by mobile phones, have been extensively developed. These mobile terminals have such applications as navigating pedestrians in collaboration with the GPS system, the distribution of maps via a mobile phone network, and a display application.

The positioning utilizing GPS, however, has a problem of hindering the positioning or decreasing accuracy in locations where the GPS signals are very weak as inside buildings or where the sufficient number of supplementary satellites cannot be secured as around buildings.

As for current pedestrian navigation, outdoor services are the mainstream. However, indoor services as in department stores or underground shopping arcade have been desired earnestly, and a lot of indoor positioning systems using IC tags, infrared rays, radio waves and ultrasonic waves have been researched. Any of these indoor positioning systems, however, require developing an infrastructure, which demands considerable cost and time.

The mobile terminals capable of carrying out pedestrian navigation include those that have a geomagnetic sensor for matching the pedestrian traveling direction with the display of a map. In addition, there are mobile terminals that further include an acceleration sensor for detecting the attitude of the mobile terminals (to find an azimuth in a given attitude, it is essential to detect the attitude with the acceleration sensor).

If autonomous navigation is realized by making use of the geomagnetic sensor and acceleration sensor which have already been employed by the pedestrian navigation system, the navigation inside the building or the like will become possible without developing basic technology or without loading the mobile terminal with a new component.

The autonomous navigation using the geomagnetic sensor and acceleration sensor is disclosed in Patent Documents 1-3.

Patent Document 1 relates to a portable position detecting apparatus that improves the position detecting accuracy of a pedestrian by the autonomous navigation (a configuration including sensors for carrying out detection of the number of steps×stride, correction of the stride and detection of the moving direction) capable of detecting the moving azimuth of the pedestrian more accurately even though the GPS signals cannot be received, and adjusting the stride in accordance with the walking state. The portable position detecting apparatus detects the moving position by the calculation of "the number of steps"×stride using a pedometer; corrects the stride in accordance with the walking state obtained from the walking time per step detected by the acceleration sensor; and detects the moving direction using the geomagnetic sensor, thereby improving the accuracy of detecting the pedestrian moving position by the autonomous navigation. In this way, it enables detecting the position of the pedestrian carrying the portable position detecting apparatus at an accuracy sufficient for practical applications with increasing the accuracy of the stride even in the case where the pedestrian is in a forest or in a valley between high-rise buildings where the GPS satellite signals cannot be received.

The Patent Document 2 relates to a walking navigation system for measuring the walking navigation of a pedestrian moving inside or outside the building. The walking navigation system has a computer. An input device, which is connected to the computer and worn on the waist of the pedestrian, has a forward accelerometer and an upward accelerometer detect the forward and upward accelerations while the pedestrian is walking. A CPU in the computer calculates a cross-correlation function from the detection results, compares it with cross-correlation functions about horizontal walking, upward walking and downward walking, which are stored in a hard disk (HD) in advance, and decides one of the walking modes. In this way, it enables recognizing that the pedestrian is walking on a path with a low difference of altitude such as going up and down the stairs.

The Patent Document 3 relates to a walking direction detecting apparatus for detecting the traveling direction of a mobile unit due to walking. It calculates the variation of the acceleration component in the horizontal direction between the time when the variation of the acceleration component in the vertical direction takes the local maximum and the time when it takes the local minimum; and estimates the walking direction from the direction of the acceleration component in the horizontal direction when the variation of the acceleration component in the horizontal direction takes the local maximum.

However, the apparatuses disclosed in the foregoing Patent Documents 1 to 3 impose on a user certain restrictions such as using the mobile terminal in the condition of wearing on the waist in a prescribed attitude, or demanding calibration after wearing even though the attitude is not limited, which are not user-friendly at all.

In addition, the apparatuses disclosed in the foregoing Patent Document 3 select one of the acceleration measurement values obtained during a specified period to be used for estimating the walking direction. However, in the acceleration measurement values, noise components having nothing to do with the walking movement are easy to get mixed, and this makes it difficult to estimate the walking direction at high accuracy. As an example of the noise, the slightest contact between the sensor system and pedestrian clothing brings about measurements of large pulse-like acceleration.

Thus it is desired to enable the pedestrian navigation that allows flexible wearing of the mobile terminal during the navigation, and does not impose a stress on the pedestrian (user).

The present invention is implemented to solve the foregoing problems. Therefore it is an object of the present invention to provide a traveling direction measuring apparatus and traveling direction measuring method capable of being used as the pedestrian navigation system at locations where it is difficult to obtain high positioning accuracy as inside buildings or around multistory buildings in which GPS is not applicable.

Patent Document 1: Japanese Patent Laid-open No. 2000-97722;

Patent Document 2: Japanese Patent Laid-open No. 2002-139340; and

Patent Document 3: Japanese Patent Laid-open No. 2003-302419.

DISCLOSURE OF THE INVENTION

The present invention is implemented to achieve such an object. The invention is a traveling direction measuring apparatus including 3-axes acceleration detecting means for detecting acceleration, and acceleration data acquiring means for 3-axes acceleration data repeatedly by a number of prescribed times or more, said 3-axes acceleration data varies with walking of a pedestrian, the traveling direction measuring apparatus being characterized by comprising: first gravity acceleration calculating means for calculating, when the pedestrian is walking with holding the traveling direction measuring apparatus in a generally fixed attitude, gravity acceleration by averaging acceleration data sets during several steps obtained by the acceleration data acquiring means; frequency component calculating means for calculating frequency components corresponding to duration of one step of the acceleration data sets projected on a plane perpendicular to the gravity acceleration calculated by the first gravity acceleration calculating means; and first moving direction estimating means for estimating a moving direction of the pedestrian seen from a terminal coordinate system associated with the traveling direction measuring apparatus according to the frequency components.

The invention is the traveling direction measuring apparatus characterized by further comprising: 3-axes geomagnetism detecting means for detecting geomagnetism; geomagnetism data acquiring means for obtaining 3-axes geomagnetism data repeatedly by a number of prescribed times or more, said 3-axes geomagnetism output data varies with the walking of the pedestrian; and first walking direction estimating means for estimating, when the pedestrian is walking with holding the traveling direction measuring apparatus in a generally fixed attitude, the walking direction of the pedestrian with respect to a terrestrial coordinate system from geomagnetism data sets obtained by the geomagnetism data acquiring means and the moving direction of the pedestrian estimated by the first moving direction estimating means.

The invention is a traveling direction measuring apparatus including 3-axes acceleration detecting means for detecting acceleration, and acceleration data acquiring means for obtaining 3-axes acceleration data repeatedly by a number of prescribed times or more, said 3-axes acceleration data varies with walking of a pedestrian, said traveling direction measuring apparatus comprising: second gravity acceleration calculating means for calculating, when the pedestrian is walking with holding and swinging said traveling direction measuring apparatus, gravity acceleration seen from a coordinate system associated with said traveling direction measuring apparatus at the time when the swing is at a lowest point based on a frequency component corresponding to duration of one step of the acceleration norm data sets calculated by individual acceleration data obtained by said acceleration data acquiring means, and frequency component corresponding to duration of one step of the acceleration data sets obtained by said acceleration data acquiring means; frequency component calculating means for calculating frequency components corresponding to duration of two steps of the acceleration data sets projected on a plane perpendicular to the gravity acceleration calculated by said second gravity acceleration calculating means; and second moving direction estimating means for estimating from the frequency component corresponding to the duration of two steps the moving direction of the pedestrian seen from a terminal coordinate system associated with said traveling direction measuring apparatus at the time when the swing is at the lowest point.

The invention is the traveling direction measuring apparatus characterized by further comprising: 3-axes geomagnetism detecting means for detecting geomagnetism; geomagnetism data acquiring means for obtaining 3-axes geomagnetism data repeatedly by a number of prescribed times or more, said 3-axes geomagnetism data varies with the walking of the pedestrian; and second walking direction estimating means for estimating, when the pedestrian is walking with holding and swinging the traveling direction measuring apparatus, the walking direction of the pedestrian with respect to a terrestrial coordinate system from geomagnetism data at the time when the swing is at the lowest point, which is obtained by the geomagnetism data acquiring means, and from the moving direction of the pedestrian estimated by the second moving direction estimating means.

The invention is a traveling direction measuring apparatus including 3-axes acceleration detecting means for detecting acceleration, and acceleration data acquiring means for obtaining 3-axes acceleration data repeatedly by a number of prescribed times or more, said 3-axes acceleration data varies with walking of a pedestrian, said traveling direction measuring apparatus comprising: first gravity acceleration calculating means for calculating, when the pedestrian is walking with holding said traveling direction measuring apparatus in a generally fixed attitude, gravity acceleration by averaging acceleration data sets during several steps obtained by said acceleration data acquiring means; frequency component calculating means for calculating frequency components corresponding to duration of one step of the acceleration data sets projected on a plane perpendicular to the gravity acceleration calculated by said first gravity acceleration calculating means; first moving direction estimating means for estimating a moving direction of the pedestrian seen from a terminal coordinate system associated with said traveling direction measuring apparatus according to the frequency components; second gravity acceleration calculating means for calculating, when the pedestrian is walking with holding and swinging said traveling direction measuring apparatus, gravity acceleration seen from the coordinate system associated with said traveling direction measuring apparatus at the time when the swing is at a lowest point based on a frequency component corresponding to duration of one step of the acceleration norm data sets calculated by individual acceleration data obtained by said acceleration data acquiring means, and frequency component corresponding to duration of one step of the acceleration data sets obtained by said acceleration data acquiring means; frequency component calculating means for calculating frequency components corresponding to duration of two steps of the acceleration data sets projected on a plane perpendicular to the gravity acceleration calculated by said second gravity acceleration calculating means; second moving direction estimating means for estimating from the frequency component corresponding to the duration of two steps the moving direction of the pedestrian seen from the terminal coordinate system associated with said traveling direction measuring apparatus at the time when the swing is at the lowest point; 3-axes geomagnetism detecting means for detecting geomagnetism; geomagnetism data acquiring means for obtaining 3-axes geomagnetism data repeatedly by a number of prescribed times or more, said 3-axes geomagnetism data varies with the walking of the pedestrian; first walking direction estimating means for estimating, when the pedestrian is walking with holding said traveling direction measuring apparatus in a generally fixed attitude, the walking direction of the pedestrian with respect to a terrestrial coordinate system from geomagnetism data sets obtained by said geomagnetism data acquiring means and the moving direction of the pedestrian estimated by said first moving direction estimating means; and second walking direction estimating means for estimating, when the pedestrian is walking with holding and swinging said traveling direction measuring apparatus, the walking direction of the pedestrian with respect to the terrestrial coordinate system from geomagnetism data at the time when the swing is at the lowest point, which is obtained by said geomagnetism data acquiring means, and from the moving direction of the pedestrian estimated by said second moving direction estimating means.

The invention is a traveling direction measuring method in a traveling direction measuring apparatus including 3-axes acceleration detecting means for detecting acceleration, and acceleration data acquiring means for obtaining 3-axes acceleration data repeatedly by a number of prescribed times or more, said 3-axes acceleration data varies with walking of a pedestrian, the traveling direction measuring method being characterized by comprising: a first gravity acceleration calculating step of calculating, when the pedestrian is walking with holding the traveling direction measuring apparatus in a generally fixed attitude, gravity acceleration by averaging acceleration data sets during several steps obtained by the acceleration data acquiring means; a frequency component calculating step of calculating frequency components corresponding to duration of one step of the acceleration data sets projected on a plane perpendicular to the gravity acceleration calculated at the first gravity acceleration calculating step; and a first moving direction estimating step of estimating a moving direction of the pedestrian seen from a terminal coordinate system associated with the traveling direction measuring apparatus according to the frequency components.

The invention is the traveling direction measuring method in the traveling direction measuring apparatus characterized by further comprising: a 3-axes geomagnetism detecting step of detecting geomagnetism; a geomagnetism data acquiring step of obtaining 3-axes geomagnetism data repeatedly by a number of prescribed times or more, said 3-axes geomagnetism data varies with the walking of the pedestrian; and a first walking direction estimating step of estimating, when the pedestrian is walking with holding the traveling direction measuring apparatus in a generally fixed attitude, the walking direction of the pedestrian with respect to a terrestrial coordinate system from geomagnetism data sets obtained at the geomagnetism data acquiring step and the moving direction of the pedestrian estimated at the first moving direction estimating step.

The invention is a traveling direction measuring method in a traveling direction measuring apparatus including 3-axes acceleration detecting means for detecting acceleration, and acceleration data acquiring means for obtaining 3-axes acceleration data repeatedly by a number of prescribed times or more, said 3-axes acceleration data varies with walking of a pedestrian, said traveling direction measuring method comprising: a second gravity acceleration calculating step of calculating, when the pedestrian is walking with holding and swinging said traveling direction measuring apparatus, gravity acceleration seen from a coordinate system associated with said traveling direction measuring apparatus at the time when the swing is at a lowest point based on a frequency component corresponding to duration of one step of the acceleration norm data sets calculated by individual acceleration data obtained by said acceleration data acquiring means, and frequency component corresponding to duration of one step of the acceleration data sets obtained by said acceleration data acquiring means; a frequency component calculating step of calculating frequency components corresponding to duration of two steps of the acceleration data sets projected on a plane perpendicular to the gravity acceleration calculated at the second gravity acceleration calculating step; and a second moving direction estimating step of estimating from the frequency component corresponding to the duration of two steps the moving direction of the pedestrian seen from a terminal coordinate system associated with said traveling direction measuring apparatus at the time when the swing is at the lowest point.

The invention is in the invention as described in claim 8 a traveling direction measuring method in the traveling direction measuring apparatus characterized by further comprising: a 3-axes geomagnetism detecting step of detecting geomagnetism; a geomagnetism data acquiring step of obtaining 3-axes geomagnetism data repeatedly by a number of prescribed times or more, said 3-axes geomagnetism data varies with the walking of the pedestrian; and a second walking direction estimating step of estimating, when the pedestrian is walking with holding and swinging the traveling direction measuring apparatus, the walking direction of the pedestrian with respect to a terrestrial coordinate system from geomagnetism data at the time when the swing is at the lowest point, which is obtained at the geomagnetism data acquiring step, and from the moving direction of the pedestrian estimated at the second moving direction estimating step.

The present invention provides the traveling direction measuring apparatus and traveling direction measuring method usable as the pedestrian navigation system in locations where it is difficult to obtain high positioning accuracy such as inside buildings or around multistory buildings where GPS cannot be used. Thus, it enables the pedestrian autonomous navigation with the mobile terminal including the geomagnetic sensor and acceleration sensor, thereby being able to implement the pedestrian navigation system and navigation method without putting the user under stress.

BEST MODE FOR CARRYING OUT THE INVENTION

The best mode for carrying out the invention will now be described with reference to the accompanying drawings to explain the present invention in more detail.

Figure 1:
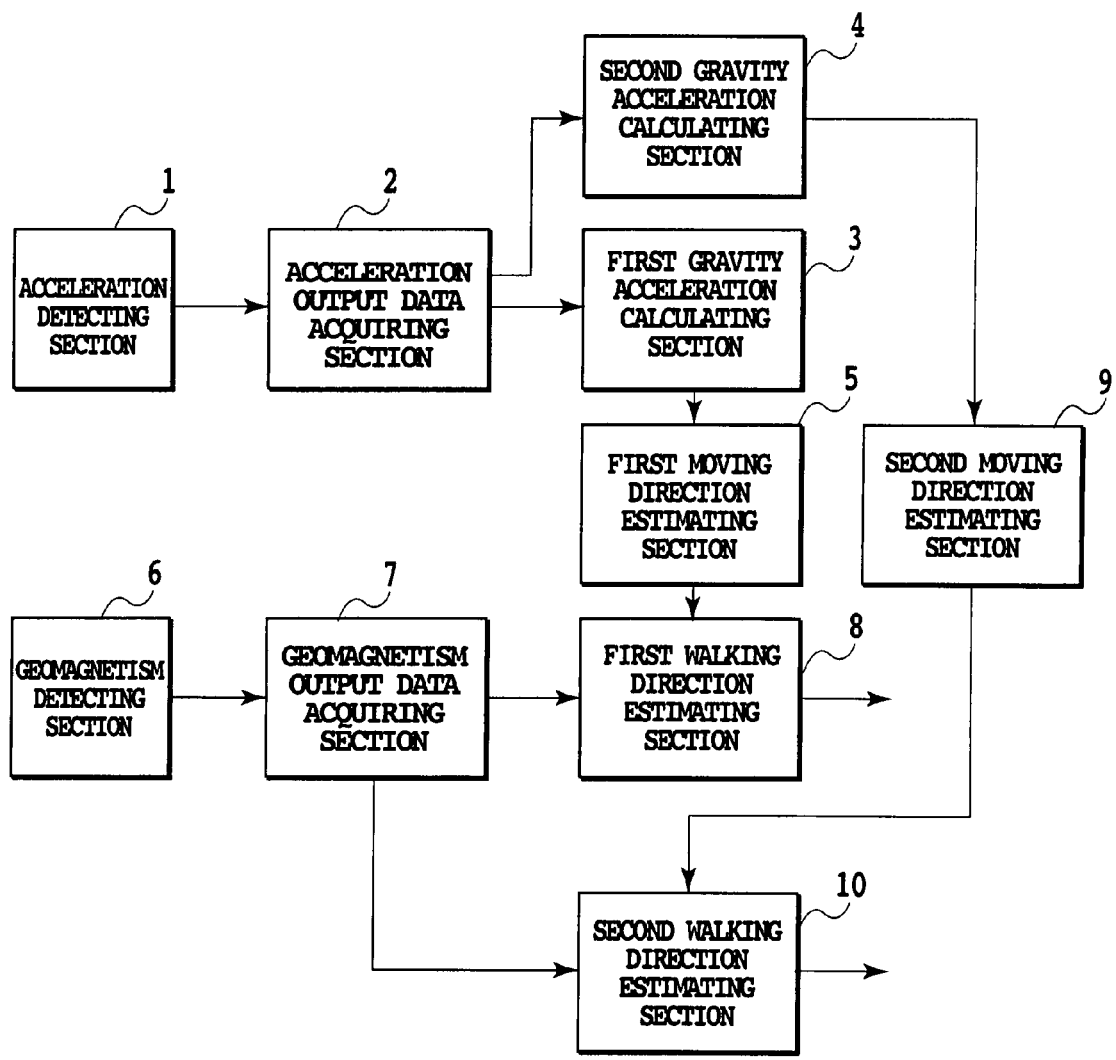
FIG. 1 is a block diagram showing a configuration of an embodiment of a traveling direction measuring apparatus in accordance with the present invention.

FIG. 1 is a block diagram showing a configuration of an embodiment of a traveling direction measuring apparatus in accordance with the present invention. In FIG. 1, the reference numeral 1 designates a 3-axes acceleration detecting section, the reference numeral 2 designates an acceleration data acquiring section, the reference numeral 3 designates a first gravity acceleration calculating section, the reference numeral 4 designates a second gravity acceleration calculating section, the reference numeral 5 designates a first moving direction estimating section, the reference numeral 6 designates a 3-axes geomagnetism detecting section, the reference numeral 7 designates a geomagnetism data acquiring section, the reference numeral 8 designates a first walking direction estimating section, the reference numeral 9 designates a second moving direction estimating section, and the reference numeral 10 designates a second walking direction estimating section.

The 3-axes acceleration detecting section 1, detects the 3-axes acceleration of the traveling direction measuring apparatus, which varies with the walking of the pedestrian. The acceleration data acquiring section 2 acquires repeatedly by the number of prescribed times or more the 3-axes acceleration data which is detected by the 3-axes acceleration detecting section 1 and varies with the walking of the pedestrian.

The first gravity acceleration calculating section 3 calculates, when the pedestrian is walking with keeping the generally fixed attitude of the traveling direction measuring apparatus, the gravity acceleration by averaging acceleration data sets during several steps which are obtained by the acceleration data acquiring section 2.

The second gravity acceleration calculating section 4 calculates norms of the individual acceleration data acquired by the acceleration data acquiring section 2 when the pedestrian is walking with holding the traveling direction measuring apparatus and swinging (arms at the sides of the body). According to the frequency component corresponding to duration of a single step of the acceleration norm data set calculated and the frequency component corresponding to the single step of the acceleration data set acquired by the acceleration data acquiring section 2, the second gravity acceleration calculating section 4 calculates the direction of the gravity acceleration seen from the terminal coordinate system associated with the traveling direction measuring apparatus at the lowest point of swinging.

The first moving direction estimating section 5 estimates the moving direction of the pedestrian seen from the terminal coordinate system associated with the traveling direction measuring apparatus from the frequency component corresponding to a single step of the acceleration data set projected on a plane perpendicular to the gravity acceleration calculated by the first gravity acceleration calculating section 3.

The 3-axes geomagnetism detecting section 6 detects the geomagnetism of the traveling direction measuring apparatus held by the pedestrian, which geomagnetism varies with the walking of the pedestrian. The geomagnetism data acquiring section 7 acquires the 3-axes geomagnetism data, which is detected by the 3-axes geomagnetism detecting section 6 and varies with the walking of the pedestrian, repeatedly by the number of prescribed times or more.

The first walking direction estimating section 8 estimates the walking direction of the pedestrian with respect to the terrestrial coordinate system from the geomagnetism data set obtained by the geomagnetism data acquiring section 7 and the moving direction of the pedestrian estimated by the first moving direction estimating section 5 when the pedestrian is walking with keeping the generally fixed attitude of the traveling direction measuring apparatus.

The second moving direction estimating section 9 estimates the moving direction of the pedestrian seen from the terminal coordinate system associated with the traveling direction measuring apparatus when his or her arms are at the lowest point according to the frequency component corresponding to two-step duration of the acceleration data set which is projected on a plane perpendicular to the gravity acceleration calculated by the second gravity acceleration calculating section 4.

The second walking direction estimating section 10 estimates, when the pedestrian is walking with holding the traveling direction measuring apparatus in hand and swinging his or her arms at the sides of the body, the walking direction of the pedestrian with respect to the terrestrial coordinate system from the geomagnetism data obtained by the geomagnetism data acquiring section 7 at the time when the arms are at the lowest point and from the moving direction of the pedestrian estimated by the second moving direction estimating section 9.

In addition, the traveling direction measuring apparatus in accordance with the present invention can have a function of the first walking direction estimating section 8 and that of the second walking direction estimating section 10.

Figure 2:
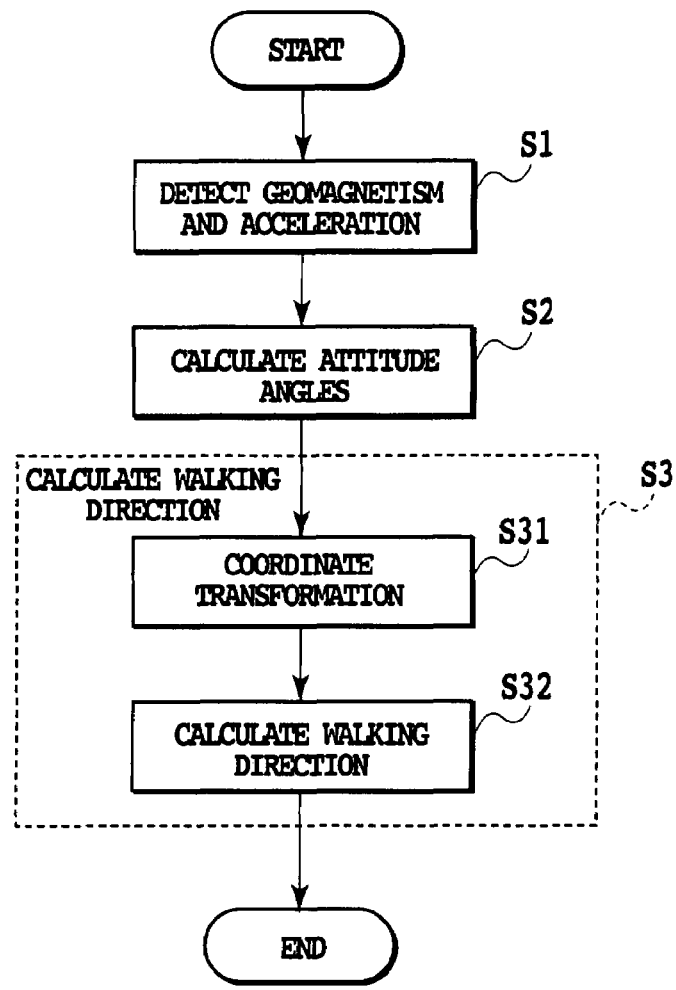
FIG. 2 is a flowchart illustrating the operation of the traveling direction measuring apparatus for implementing the autonomous navigation using a mobile terminal including a geomagnetic sensor and an acceleration sensor.

FIG. 2 is a flowchart illustrating the operation of the traveling direction measuring apparatus for implementing the autonomous navigation using the mobile terminal including the geomagnetic sensor and acceleration sensor.

First, the geomagnetic sensor and the acceleration sensor mounted on the mobile terminal detect the geomagnetism and acceleration during walking (S1). Generally, an algorithm for estimating the walking direction varies according to the carrying state of the mobile terminal. The term "carrying state of the mobile terminal" is considered to refer to various states: a state in which the attitude of the mobile terminal during walking is generally fixed such as when the pedestrian is walking viewing a screen displaying a map during the navigation or walking with the mobile terminal putting in a pocket; a state in which the pedestrian holds the mobile terminal in hand and swings his or her arms at the sides of the body; and a state in which the mobile terminal is placed in a bag.

Figure 3:
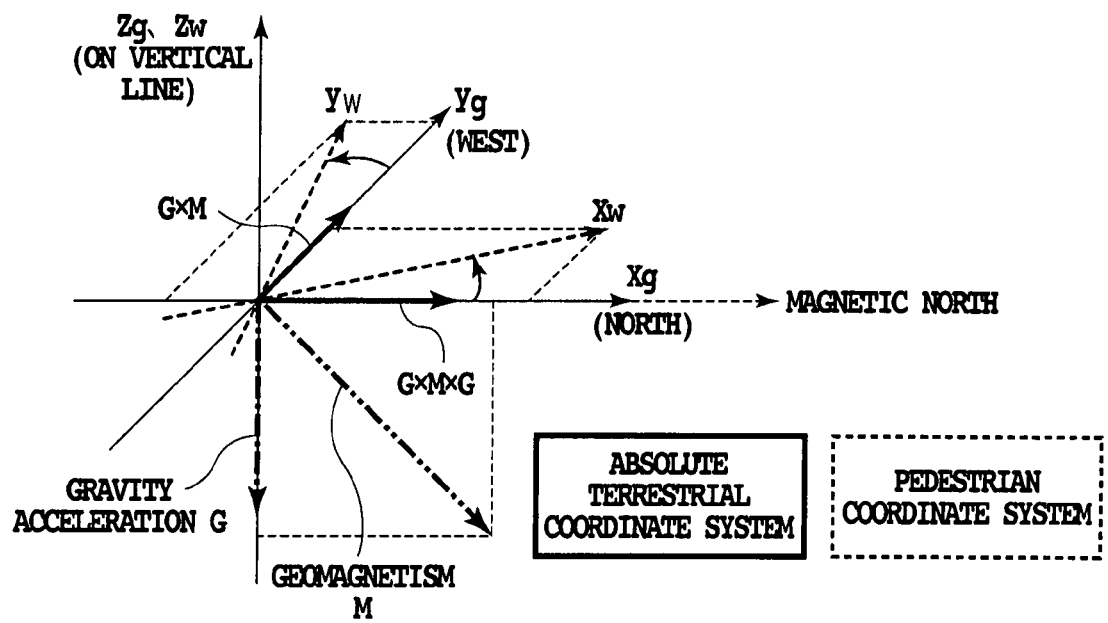
FIG. 3 is a diagram illustrating relationships between a pedestrian coordinate system and an absolute terrestrial coordinate system.

Subsequently, according to a series of acceleration data sets obtained, the attitude angles of the mobile terminal are calculated (S2). Considering the case where the pedestrian is walking viewing the map screen, he or she can watch the screen in a vertical or horizontal state. Different attitude angles will result in different measured values of the geomagnetism and acceleration which are measured with respect to the coordinate system fixed to the terminal. FIG. 3 is a diagram illustrating relationships between the pedestrian coordinate system and the absolute terrestrial coordinate system. The attitude angles generally means the attitude with respect to a coordinate system consisting of the gravity and geomagnetism as shown in FIG. 3 (an absolute terrestrial coordinate system defined as a coordinate system having the north-south direction as an x axis (northward is positive), the east-west direction as a y axis (westward is positive), and the vertical direction as z axis (upward is positive)). Strictly speaking, however, its definition differs according to the carrying state of the mobile terminal. For example, when the mobile terminal is generally fixed as when the pedestrian is walking viewing the map screen, the definition of the attitude angles is simple because there are no fluctuations in the attitude. However, in the case where the pedestrian holds the mobile terminal in hand swinging at the side of his or her body, since the attitude varies every moment, the attitude is defined at a specially fixed point of time. The specially fixed point of time can be defined as a moment the arms pass the lowest point, for example.

Subsequently, the calculation of the walking direction is carried out (S3). After the attitude is estimated, a series of geomagnetism data sets and acceleration data sets acquired are converted to measured values on the absolute terrestrial coordinate system to enable evaluation of the measured values in the same attitude without fail (referred to as "converted measured values" from now on: S31).

According to the algorithm prepared for each carrying state of the mobile terminal during walking, the geomagnetism measurement values and acceleration measurement values after the conversion are processed, and the pedestrian traveling direction is calculated (S32).

Furthermore, a walking distance can be calculated by multiplying the number of steps by the stride, for example, and combining it with the walking direction can provide the relative moving position, enabling the autonomous navigation.

Thus, the pedestrian navigation system mounting the GPS can not only correct the current position more precisely by updating the current position in accordance with the information obtained from the GPS when the positioning by the GPS succeeds or by correcting the current position by the autonomous navigation when the positioning by the GPS is not carried out, but also continue the navigation in locations where the GPS signals cannot be received such as inside or around the buildings, or in locations where it is difficult to obtain high positioning accuracy.

When the pedestrian is walking using the pedestrian navigation system, two types of the carrying states of the mobile terminal are considered to be dominant. One of them is walking holding the mobile terminal in hand and checking the map displayed on the mobile terminal; and the other is walking swinging his or her arms with holding the mobile terminal in hand up to a marked position after the checking. Accordingly, as long as the traveling direction can be estimated in the above-mentioned two types of the carrying states of the mobile terminal, the autonomous navigation can be implemented in considerable duration in the walking.

Next, the estimation method will be described of the walking direction in the foregoing two conditions: 1) walking with holding the mobile terminal in hand or the like in generally fixed attitude; and 2) walking with holding the mobile terminal in hand and swinging his or her arms.

When Walking with Generally Fixed Attitude>

Figure 4:
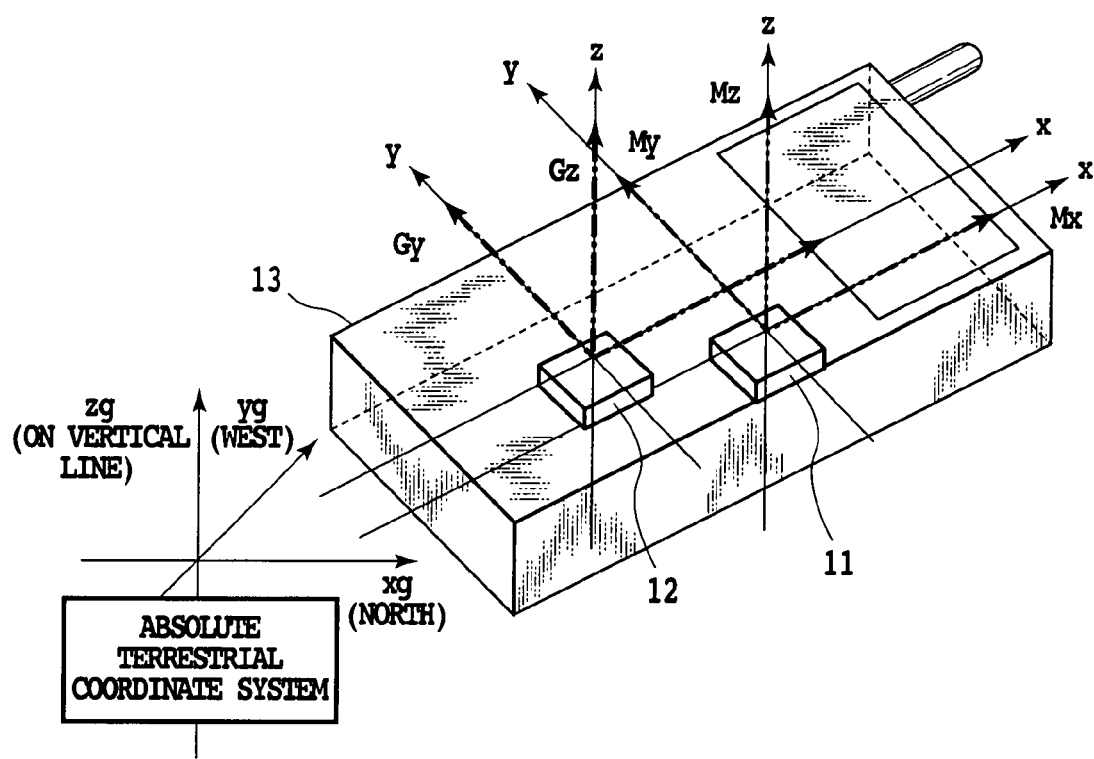
FIG. 4 is a diagram illustrating relationships between a terminal coordinate system and the absolute terrestrial coordinate system.
Figure 5A:
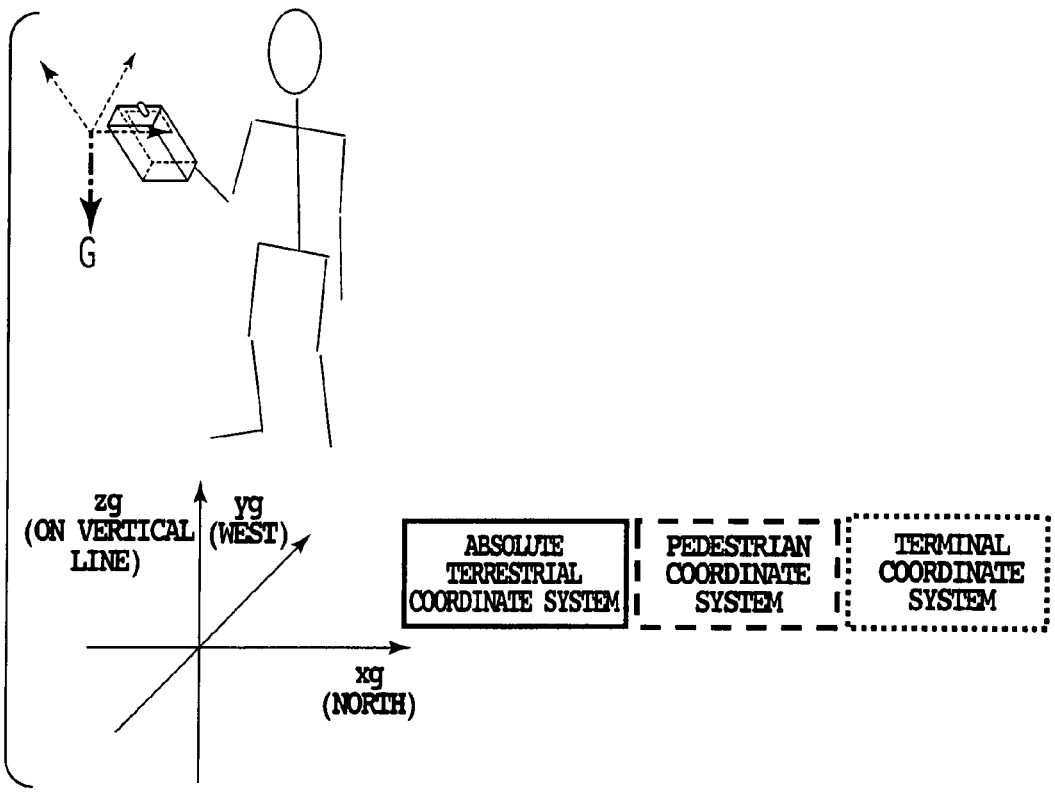
FIG. 5A is a diagram showing a pedestrian walking image in the case where the attitude of a mobile terminal is generally fixed.
Figures 5B, 5C, 5D:
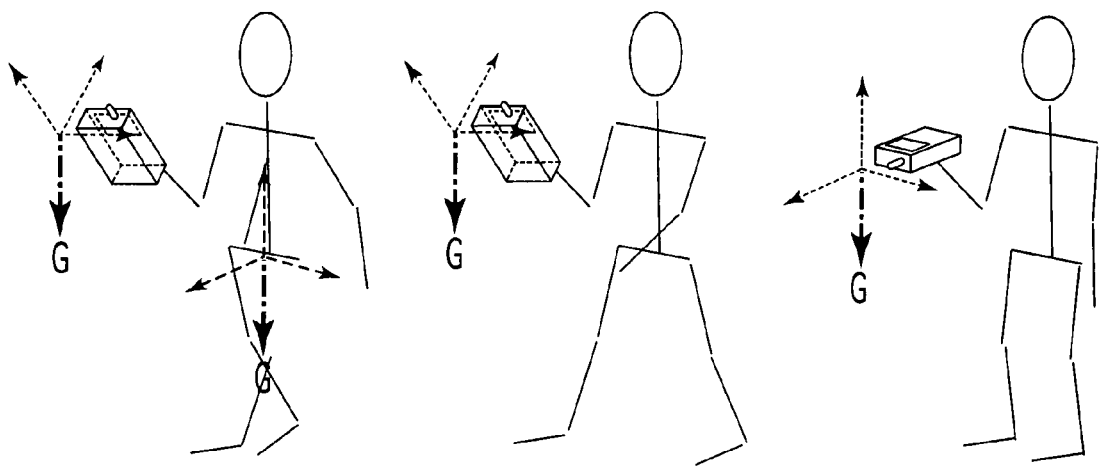
FIG. 5B is a diagram showing a pedestrian walking image in the case where the attitude of the mobile terminal is generally fixed.
FIG. 5C is a diagram showing a pedestrian walking image in the case where the attitude of the mobile terminal is generally fixed.
FIG. 5D is a diagram showing a pedestrian walking image in the case where the attitude of the mobile terminal is generally fixed.

A 3-axes Cartesian coordinate system will be described which is fixed to the pedestrian and has the pedestrian traveling direction as the x axis, an axis orthogonal to the traveling direction in a horizontal plane as the y axis, and the vertical direction as the z axis. The 3-axes Cartesian coordinate system fixed to the pedestrian is referred to as the pedestrian coordinate system from now on. The mobile terminal is fixed in an arbitrary attitude with respect to the pedestrian coordinate system. The coordinate system of the mobile terminal (that is, the coordinate system consisting of the measurement axes of the geomagnetic sensor and acceleration sensor) is referred to as a terminal coordinate system. FIG. 4 is a diagram illustrating relationships between the terminal coordinate system and the absolute terrestrial coordinate system. In FIG. 4, the reference numeral 11 designates the 3-axes geomagnetic sensor, the reference numeral 12 designates the 3-axes acceleration sensor, and the reference numeral 13 designates the navigation system.

Next, the acceleration seen from the pedestrian coordinate system will be described.

Figure 7:
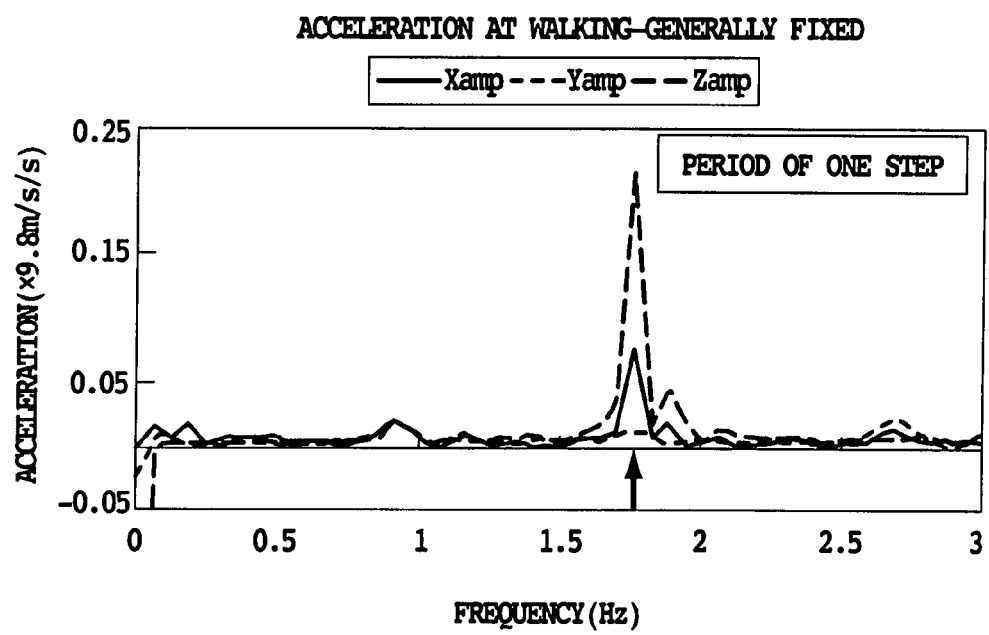
FIG. 7 is a diagram illustrating frequency spectra of acceleration measurement values when the user walks with generally fixing the terminal coordinate system to the pedestrian coordinate system.

FIG. 5A to FIG. 5D are diagrams showing a walking image of the pedestrian with generally fixing the attitude of the mobile terminal. The relationships between the terminal coordinate system and the pedestrian coordinate system are generally consistent during walking. During the normal walking, the moving acceleration is generally measured as follows in the pedestrian coordinate system. More specifically, the dominant acceleration is the acceleration in the vertical direction (z axis), and is observed in terms of periodic data with a period of the time taken by each step (see Zamp of FIG. 7). The acceleration in the traveling direction (x axis) has both acceleration direction and deceleration direction at each step, and is observed in terms of periodic data with a period of one step (see Xamp of FIG. 7). It has been confirmed by experiment that the component with a period of one step of the acceleration in the traveling direction and that of the acceleration in the vertical direction have a phase difference of about 90 degrees in general. The acceleration in the lateral direction (y axis) swings in opposite directions step by step, and hence is observed in terms of periodic data with a period of two steps (see Yamp of FIG. 7). The component with a period of one step of the acceleration in the lateral direction is small. FIG. 7 illustrates frequency spectra of the accelerations in the individual directions (vertical direction, traveling direction, and lateral direction), which are measured in the terminal coordinate system when the pedestrian is walking with generally matching the pedestrian coordinate system with the terminal coordinate system (when walking with keeping the attitude of FIG. 5D).

Next, the traveling direction of the pedestrian seen from the terminal coordinate system will be described.

In the terminal coordinate system, if the vertical direction component of the frequency component with a period of one step of the acceleration measured can be eliminated, the direction, in which the frequency component with a period of the remaining one step is strongest, is the traveling direction seen from the pedestrian terminal coordinate system (at this point of time, although a flow line is found, its direction is not). In addition, the direction (of the flow line) can be found by comparing the phase of the frequency component with a period of one step of the acceleration in the vertical direction with the phase of the frequency component with a period of one step of the acceleration other than in the vertical direction (that is, the acceleration in the traveling direction). When used in the pedestrian navigation, it calculates the walking direction of the pedestrian by converting traveling direction seen from the terminal coordinate system to the direction seen from the absolute terrestrial coordinate system.

Next, the attitude angles of the terminal coordinate system with respect to the absolute terrestrial coordinate system will be described.

To eliminate the vertical direction component from the acceleration measured on the terminal coordinate system, the vertical direction seen from the terminal coordinate system must be found. In addition, to carry out the pedestrian navigation, the direction seen from the absolute terrestrial coordinate system must be found. More specifically, the relationships of the terminal coordinate system with respect to the absolute terrestrial coordinate system, that is, the attitude angles are necessary.

Next, the calculation of the attitude angles will be described.

The attitude angles of the terminal coordinate system with respect to the absolute terrestrial coordinate system can be obtained as follows. More specifically, if the pedestrian is walking on a line constantly, although the speed varies during each step, the average speed of each step is invariant. In addition, since it is assumed that the mobile terminal has a generally fixed attitude, the integral of the acceleration during each step of the moving acceleration among the accelerations measured on the terminal coordinate system (the result obtained by subtracting the gravity acceleration from all the accelerations measured) becomes zero (because unless it is zero, the walking speed varies step by step). More specifically, when all the accelerations (gravity acceleration+moving acceleration) measured on the terminal coordinate system are integrated during one step, only the gravity acceleration remains. From the gravity acceleration G thus obtained and the geomagnetism M, the attitude of the mobile terminal can be calculated. As for the geomagnetism M, since it can be considered to little vary during walking on a line, it is possible to adopt a measured value at an appropriate point of time as a typical value, or to use the average value in a specified period. Unit vectors $e_x$, $e_y$, $e_z$ representing the x, y, z coordinate axes of the terminal coordinate system seen from the absolute terrestrial coordinate system are given by the following expression.

[expression 1]

$$Z = [e_x \ e_y \ e_z] = \left[ \frac{G \times M \times G}{|M| \cdot |G|^2} \quad \frac{M \times G}{|M| \cdot |G|} \quad \frac{-G}{|G|} \right] \quad (1)$$

Next, the calculation of the walking direction will be described.

After the attitude is obtained, the acceleration measured on the terminal coordinate system undergoes coordinate transformation to the value measured on the absolute terrestrial coordinate system. The value $x_U$ measured on the terminal coordinate system is transformed to the value $x_g$ measured on the absolute terrestrial coordinate system by the following expression.

[expression 2]

$$x_g = Z^T x_U \quad (2)$$

The Z component of the acceleration passing through the coordinate transformation is the acceleration in the vertical direction. When calculating the frequency components with a period of one step of the X and Y components of the acceleration passing through the coordinate transformation, the direction indicated by the ratio of the amplitudes gives the walking direction of the pedestrian (flow line). In addition, by comparing the phase of the frequency component with a period of one step of the Z component of the acceleration passing through the coordinate transformation with the phase of the frequency component with a period of one step of the X and Y components, the direction of the pedestrian walking is found. Applying Fourier transform to the acceleration $a_g$ transformed to the absolute terrestrial coordinate system, and placing the amplitude of the frequency component corresponding to the duration of one step obtained as $A_x$, $A_y$, $A_z$, and the phase thereof as $f_x$, $f_y$, $f_z$, then the traveling direction $\theta_d$ is calculated by the following expression.

[expression 3]

$$\theta_d = \mathrm{Tan}^{-1}\left( \frac{\mathrm{sgn}(\varphi_y - \varphi_z - \pi) A_y}{\mathrm{sgn}(\varphi_x - \varphi_z - \pi) A_x} \right) \quad (3)$$

The foregoing method is little affected by instantaneous noise because it estimates the traveling direction using the amplitude and phase calculated from the measured value sets during at least one step.

<When Swinging Terminal>

Subsequently, the acceleration seen from the terminal coordinate system will be described when the pedestrian is walking in such a manner that the terminal coordinate system agrees with the pedestrian coordinate system when his or her arms come to the lowest point.

Figure 6A:
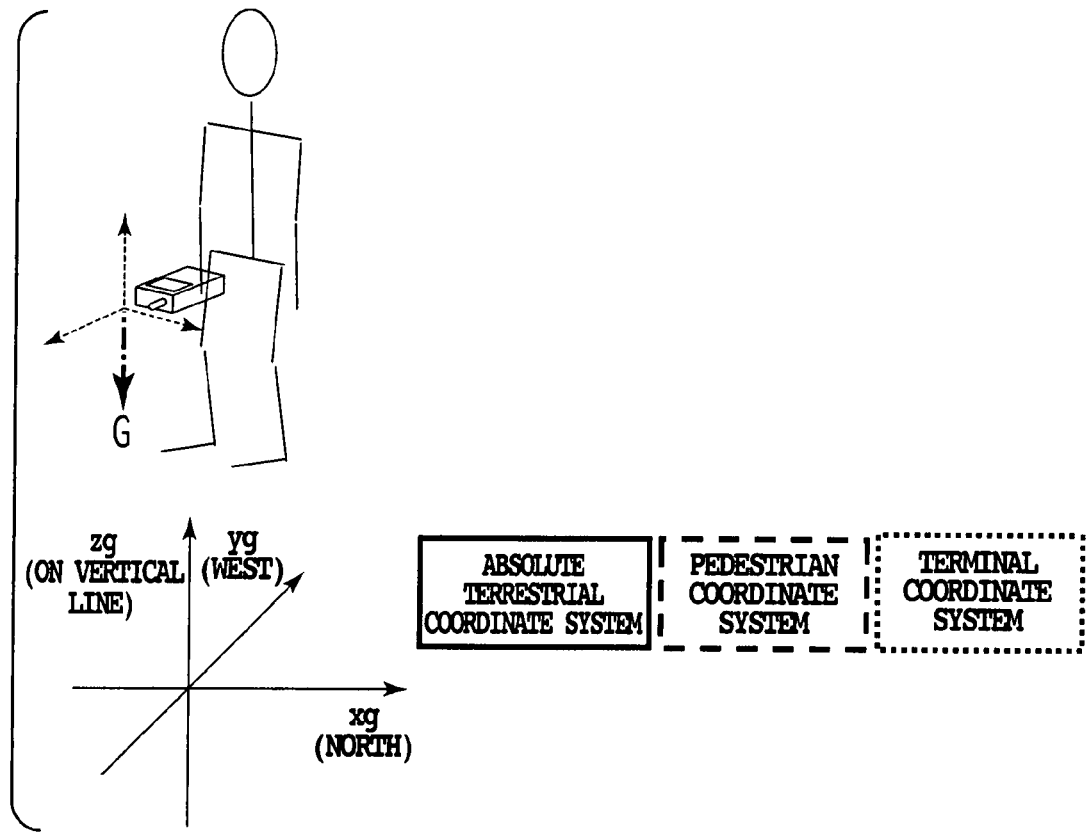
FIG. 6A is a diagram showing the case where a user walks with holding a mobile terminal in hand and swinging arms.
Figure 6B:
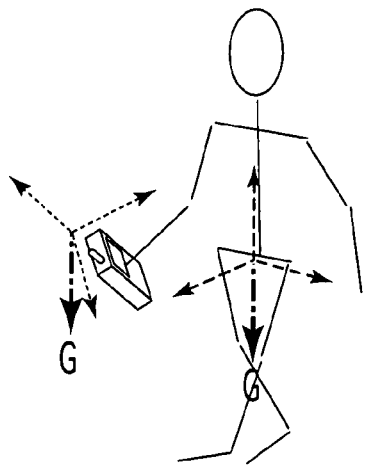
FIG. 6B is a diagram showing the case where the user walks with holding the mobile terminal in hand and swinging arms.
Figure 6C:
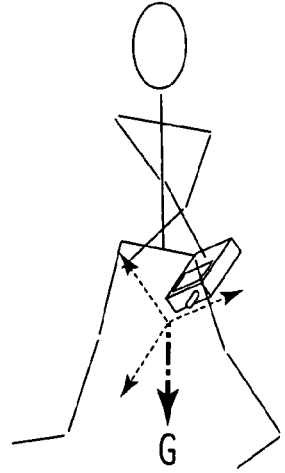
FIG. 6C is a diagram showing the case where the user walks with holding the mobile terminal in hand and swinging arms.

FIG. 6A to FIG. 6C are diagrams showing the case where the user is walking swinging his or her arms with holding the mobile terminal in hand. The mobile terminal performs pendular movement seen from the pedestrian coordinate system. As shown in FIG. 6A, it is assumed that the terminal coordinate system agrees with the pedestrian coordinate system in the condition that the pedestrian lowers his or her arms with holding the mobile terminal in hand. Then assuming that the pedestrian starts walking from this state, and passes through this state (in which the terminal coordinate system agrees with the pedestrian coordinate system) periodically during walking, the moving acceleration is generally measured as follows in the terminal coordinate system.

Figure 8:
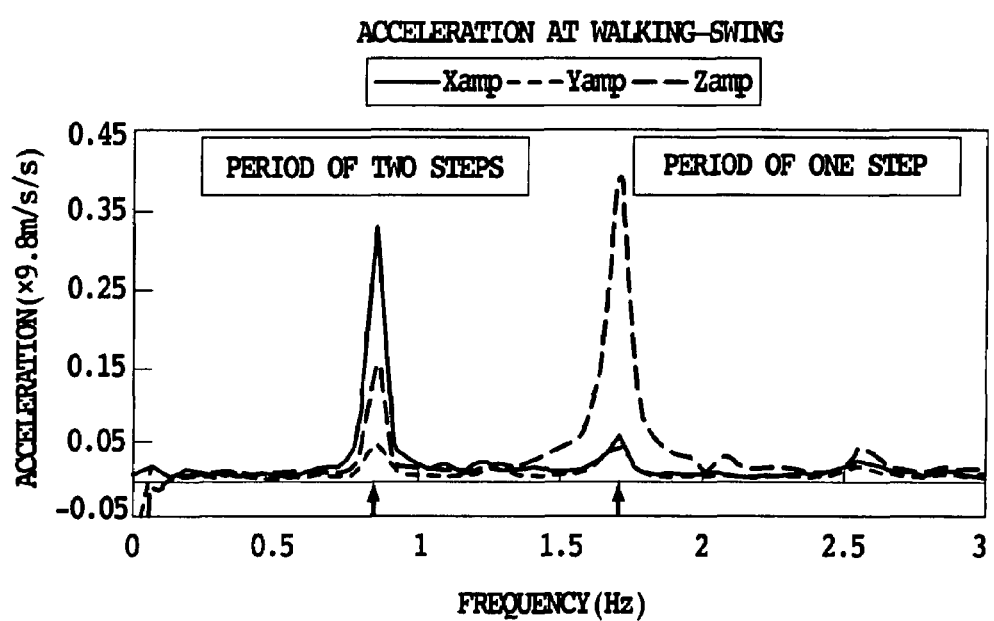
FIG. 8 is a diagram illustrating frequency spectra of acceleration measurement values when the user walks with bringing the terminal coordinate system at the lowest point into agreement with the pedestrian coordinate system, and holding the mobile terminal in swinging arm.

The user arms carry out the pendular movement, and the acceleration of the Z component of the terminal coordinate system passes through the lowest point each step of walking. Thus, the frequency component with a period of one step is predominant (see Zamp of FIG. 8). As for the other (X, Y) components, however, as seen from the fact that the arms pass through the lowest point in the same direction once per two steps, the measured values become periodic data with a period of two steps basically (see Xamp and Yamp of FIG. 8). The Y (lateral direction) component, which results from the right and left swing at the pedestrian walking, is usually small enough as compared with the X (traveling direction) component. It has been confirmed by experiment that the phase difference between the frequency components of the X and Z components with a period of two steps on the terminal coordinate system is generally zero degree. FIG. 8 illustrates the frequency spectra of the acceleration measurement values when the user walks swinging his or her arms with holding the mobile terminal in the state in which the terminal coordinate system at the lowest point is brought into agreement with the pedestrian coordinate system.

Next, the calculation of the attitude angles of the terminal coordinate system with respect to the absolute terrestrial coordinate system (at the time when the arms pass through the lowest point) will be described.

The pedestrian is walking swinging his or her arms with holding the mobile terminal in hand as described above. When the manner in which the pedestrian holds the mobile terminal is random, the walking direction can be estimated as follows. More specifically, the frequency components $(a_x, f_x)$, $(a_y, f_y)$, $(a_z, f_z)$ with a period of one step of the acceleration measurement values of the individual axes and the frequency component $(N, f_N)$ corresponding to the duration of one step of the norm of the acceleration measurement values are calculated, first, and the value obtained by the following expression is made the gravity acceleration G.

[expression 4]

$$G = \begin{pmatrix} \mathrm{sgn}(\cos(\varphi_x - \varphi_N)) \times a_x \\ \mathrm{sgn}(\cos(\varphi_y - \varphi_N)) \times a_y \\ \mathrm{sgn}(\cos(\varphi_z - \varphi_N)) \times a_z \end{pmatrix} \quad (4)$$

Subsequently, the geomagnetism at the time when the hands pass through the lowest point is designated by M. The following expression gives the attitude of the terminal coordinate system with respect to the absolute terrestrial coordinate system when the arms pass through the lowest point.

[expression 5]

$$Z = [e_x\ e_y\ e_z] = \left[ \frac{G \times M \times G}{|M| \cdot |G|^2} \quad \frac{M \times G}{|M| \cdot |G|} \quad \frac{-G}{|G|} \right] \quad (5)$$

Next, the calculation of the walking direction will be described.

After the attitude is obtained, the acceleration measured on the terminal coordinate system undergoes coordinate transformation to the value measured on the absolute terrestrial coordinate system. The value $x_U$ measured on the terminal coordinate system is transformed to the value $x_g$ measured on the absolute terrestrial coordinate system by the following expression.

[expression 6]

$$x_g = Z^T x_U \quad (6)$$

When calculating the frequency components with a period of two steps of the X and Y components of the acceleration passing through the coordinate transformation, the direction indicated by the ratio between the amplitudes gives the walking direction of the pedestrian. In addition, by comparing the phase of the frequency component with a period of one step of the Z component of the acceleration passing through the coordinate transformation with the phase of the frequency component with a period of two steps of the X and Y components, the direction of the pedestrian walking is found. Applying Fourier transform to the acceleration $a_g$ transformed to the absolute terrestrial coordinate system, and placing the amplitude of the frequency component corresponding to the duration of two steps obtained as $A_x, A_y, A_z$, and the phase thereof as $f_x, f_y, f_z$, then the traveling direction $\theta_d$ is calculated by the following expression.

[expression 7]

$$\theta_d = \mathrm{Tan}^{-1}\left( \frac{\mathrm{sgn}(\cos(\varphi_y - \varphi_z))A_y}{\mathrm{sgn}(\cos(\varphi_x - \varphi_z))A_x} \right) \quad (7)$$

The foregoing method is little affected by instantaneous noise because it estimates the traveling direction using the amplitude and phase calculated from the measured value sets during at least two steps.

INDUSTRIAL APPLICABILITY

The present invention provides the traveling direction measuring apparatus and traveling direction measuring method that can be used as the pedestrian navigation system in locations where it is difficult to obtain high positioning accuracy such as inside buildings or around multistory buildings where GPS cannot be used. Thus, it enables the pedestrian autonomous navigation with the mobile terminal including the geomagnetic sensor and acceleration sensor, thereby being able to implement the pedestrian navigation system and navigation method without putting the user under stress.

The invention claimed is:

1. A traveling direction measuring apparatus including 3-axes acceleration detecting means for detecting acceleration, and acceleration data acquiring means for obtaining 3-axes acceleration data repeatedly by a number of prescribed times or more, said 3-axes acceleration data varies with walking of a pedestrian, said traveling direction measuring apparatus comprising:
   first gravity acceleration calculating means for calculating, when the pedestrian is walking with holding said traveling direction measuring apparatus in a generally fixed attitude, gravity acceleration by averaging acceleration data sets during several steps obtained by said acceleration data acquiring means;
   frequency component calculating means for calculating frequency components corresponding to duration of one step of the acceleration data sets projected on a plane perpendicular to the gravity acceleration calculated by said first gravity acceleration calculating means;
   first moving direction estimating means for estimating a moving direction of the pedestrian seen from a terminal coordinate system associated with said traveling direction measuring apparatus according to the frequency components;
   frequency component calculating means for calculating, when the pedestrian is walking with holding and swinging said traveling direction measuring apparatus, norms of individual acceleration data obtained by said acceleration data acquiring means, and for calculating frequency components varying during one step of the acceleration norm data sets calculated, and frequency components corresponding to duration of one step of the acceleration data sets obtained by said acceleration data acquiring means;
   second gravity acceleration calculating means for calculating, when the pedestrian is walking with holding and swinging said traveling direction measuring apparatus, gravity acceleration seen from the coordinate system associated with said traveling direction measuring apparatus at the time when the swing is at a lowest point based on a frequency component corresponding to duration of one step of the acceleration norm data sets calculated by individual acceleration data obtained by said acceleration data acquiring means, and frequency component corresponding to duration of one step of the acceleration data sets obtained by said acceleration data acquiring means;

frequency component calculating means for calculating frequency components corresponding to duration of two steps of the acceleration data sets projected on a plane perpendicular to the gravity acceleration calculated by said second gravity acceleration calculating means;

second moving direction estimating means for estimating from the frequency component corresponding to the duration of two steps the moving direction of the pedestrian seen from the terminal coordinate system associated with said traveling direction measuring apparatus at the time when the swing is at the lowest point;

3-axes geomagnetism detecting means for detecting geomagnetism; geomagnetism data acquiring means for obtaining 3-axes geomagnetism data repeatedly by a number of prescribed times or more, said 3-axes geomagnetism data varies with the walking of the pedestrian;

first walking direction estimating means for estimating, when the pedestrian is walking with holding said traveling direction measuring apparatus in a generally fixed attitude, the walking direction of the pedestrian with respect to a terrestrial coordinate system from geomagnetism data sets obtained by said geomagnetism data acquiring means and the moving direction of the pedestrian estimated by said first moving direction estimating means; and second walking direction estimating means for estimating, when the pedestrian is walking with holding and swinging said traveling direction measuring apparatus, the walking direction of the pedestrian with respect to the terrestrial coordinate system from geomagnetism data at the time when the swing is at the lowest point, which is obtained by said geomagnetism data acquiring means, and from the moving direction of the pedestrian estimated by said second moving direction estimating means.

* * * * *